United States Patent
Chou et al.

[11] Patent Number: 5,981,577
[45] Date of Patent: Nov. 9, 1999

[54] α-METHYLENE PEPEROMINS AND HALOGENATED DERIVATIVES THEREOF

[75] Inventors: Shan-Yen Chou, Taipei; Shan-Shue Wang, Tainan; Han-Jung Tsai, Taipei; Shyh-Fong Chen, Taipei; Hou Ku, Taipei, all of Taiwan

[73] Assignee: Development Center for Biotechnology, Taiwan

[21] Appl. No.: 09/205,690

[22] Filed: Dec. 4, 1998

[30] Foreign Application Priority Data

Jun. 18, 1998 [TW] Taiwan ................................. 87109807

[51] Int. Cl.[6] .......................... A61K 31/34; C07D 307/33
[52] U.S. Cl. .......................... 514/473; 549/295; 549/323; 549/324
[58] Field of Search ..................... 549/295, 323, 549/324; 514/473

[56] References Cited

PUBLICATIONS

CA 119: 138999, 1993.
Elzbieta Hejchman et al., Synthesis and Cytotoxicity of Water–Soluble Ambrosin Prodrug Candidates, J. Med. Chem., vol. 38, pp. 3407–3410 (1995).
Chiu–Ming Chen et al., Peperomins A, B and C, Novel Secolignans from *Peperomia Japonica*, Heterocycles, vol. 29, pp. 411–414 (1989).
Raymundo Cruz–Almanza et al., Stereoselective Total Synthesis of (±)–Peperomin C, Heterocycles, vol. 34, pp. 2323–2330 (1992).
Sheng–Hsu Zee et al., Synthesis of (±) Peperomins, Journal of the Chinese Chemical Society, vol. 37, pp. 583–589 (1990).
Emil J. Freireich et al., Quantitative Comparison of Toxicity of Anticancer Agents in Mouse, Rat, Hamster, Dog, Monkey and Man, Cancer Chemotherapy Reports, vol. 50, pp. 219–245 (1996).

*Primary Examiner*—Amelia Owens
*Attorney, Agent, or Firm*—Finnegan, Henderson, Farabow, Garrett & Dunner, L.L.P.

[57] ABSTRACT

A compound of formula I,

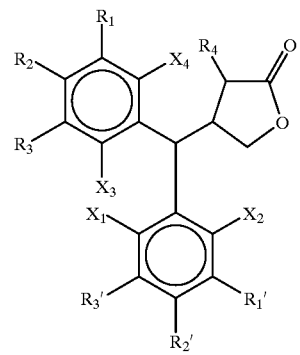

wherein $R_1$, $R_2$, $R_3$, $R_1'$, $R_2'$, and $R_3'$ are independently the same or different and each represent hydrogen, hydroxy, or lower alkoxy, or any vicinal two of $R_1$, $R_2$, $R_3$, $R_1'$, $R_2'$, and $R_3'$ combined together represent $-O-(CH_2)_n-O-$, wherein n=1 or 2; $R_4$ represents methylene or halomethyl; and $X_1$, $X_2$, $X_3$, and $X_4$ are independently the same or different and each represent hydrogen or halogen; or a pharmaceutically acceptable salt thereof. Also disclosed are a pharmaceutical composition that contains an effective amount of a compound of formula I together with a pharmaceutically acceptable excipient, and a method of treating cancer that involves the administration of an effective amount of the compound of formula I to a patient in need thereof.

24 Claims, No Drawings

α-METHYLENE PEPEROMINS AND HALOGENATED DERIVATIVES THEREOF

BACKGROUND OF THE INVENTION

1. Field of the Invention

The present invention relates to butyrolactones having potential therapeutic antitumor activity. More particularly, the present invention relates to peperomin analogs and the use thereof in treating cancer.

2. Description of Related Arts

Increasing research has been devoted to developing synthetic routes to γ-butyrolactones. This has been in large part due to interest in several biologically active natural products that have the γ-butyrolactone moiety as a major structure feature. Examples of such biologically active natural products are peperomin, ambrosin, alantolactone, and euparotin.

These naturally occurring lactones have potential therapeutic application. However, they suffer from the problem of aqueous insolubility. Recently, a number of water-soluble ambrosin derivatives have therefore been prepared for potential use as prodrugs (See, Hejchman, et al. *J. Med. Chem.* 1995, 38, 3407). The water-soluble ambrosin analogs, known to possess potent antitumor activity, were prepared by reacting ambrosin with secondary amines, sodium bisulfite, or sodium dithionite via Michael addition. It is believed that after administration the Michael adducts are converted back to ambrosin by a retro-Michael mechanism.

Peperomins A, B, and C, each a lignan having unusual seco structure, were isolated from the Chinese plant *Peperomia japonica* Makino (Piperaceae). The aqueous and alcoholic decoctions of the whole herb are used in folk medicine for treating malignant tumors. The peperomin A, B, and C series can be regarded as 2-methyl-3-di[(substituted)phenyl]methyl γ-lactone derivatives (see formula below).

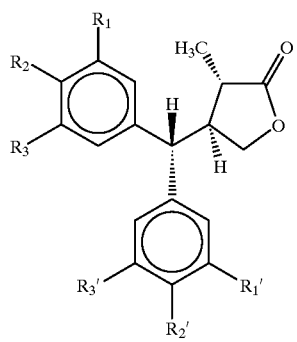

Peperomin A: $R_1$, $R_2$=—$OCH_2O$—; $R_1'$, $R_2'$=—$OCH_2O$—; $R_3$=$R_3'$=$OCH_3$ Peperomin B: $R_1$=$R_2$=$OCH_3$; $R_1'$, $R_2'$=—$OCH_2O$—

Peperomin C: $R_1$=$R_2$=$R_3$=$R_1'$=$R_2'$=$R_3'$=$OCH_3$

The isolation and synthesis of peperomins A, B, and C have been described (See, Chen, et al., *Heterocycles*, 1989, 29, 411 and Zee, et al., *Journal of the Chinese Chemical Society* 1990, 37, 583).

A problem encountered with current anticancer drugs, e.g., doxorubicin, is hypersensitivity towards leukemia cells versus other solid tumor cells.

SUMMARY OF THE INVENTION

Accordingly, one aspect of the present invention is in providing novel peperomins with improved properties.

Another aspect of the invention is in providing compounds not exhibiting hypersensitivity to MOLT-4 leukemia cell line.

Still another aspect of the invention is in providing pharmaceutical compositions containing an effective amount of the novel peperomins and a pharmaceutically acceptable excipient.

A further aspect of the invention is in providing a method of treating cancer by administering the novel peperomin analogs. A still further aspect is in providing a method of treating cancer by administering the pharmaceutical compositions containing the novel peperomin analogs.

Additional aspects of the invention will be set forth in part in the description that follows, and in part will be apparent from the description, or may be learned by the practice of the invention. The aspects of the invention will be realized and attained by means of the elements and combinations particularly pointed out in the appended claims.

The present invention provides compounds of the formula I, i.e., a series of peperomin analogs that are α-methylene-3-di[(substituted)-phenyl]methyl γ-butyrolactones and halogenated derivatives thereof:

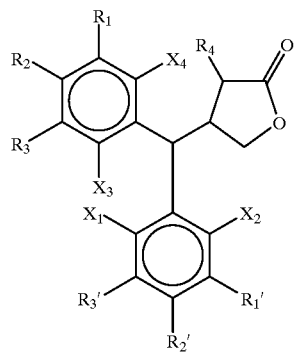

(I)

wherein $R_1$, $R_2$, $R_3$, $R_1'$, $R_2'$, and $R_3'$ are independently the same or different and each represent hydrogen, hydroxy, or lower alkoxy, or any vicinal two of $R_1$, $R_2$, $R_3$, $R_1'$, $R_2'$, and $R_3'$ combined together represent —O—$(CH_2)_n$—O—, wherein n=1 or 2; $R_4$ represents methylene or halomethyl; and $X_1$, $X_2$, $X_3$, and $X_4$ are independently the same or different and each represent hydrogen or halogen; or a salt thereof, and especially a pharmaceutically acceptable salt thereof.

Both the foregoing general description and the following detailed description of the invention are exemplary and explanatory only and are not necessarily restrictive of the claimed invention.

DETAILED DESCRIPTION OF THE INVENTION

The terms used to describe the variables in the formulas, including $R_1$ through $R_3$, $R_1'$ through $R_3'$, and $X_1$ through $X_5$, are now defined. The term lower alkyl denotes a univalent, branched or straight hydrocarbon chain containing 1 to 8 carbon atoms, preferably 1 to 4 carbon atoms. Representative examples of the lower alkyl groups include, but are not limited to, methyl, ethyl, propyl, isopropyl, butyl, sec-butyl, tert-butyl, pentyl, isopentyl, tert-pentyl, hexyl, isohexyl, and octyl.

The term halogen or halo represents chlorine, bromine, or fluorine.

The term haloalkyl denotes alkyl groups substituted with halogens, preferably fluorine, bromine, or chlorine. The alkyl groups include, but are not limited to, lower alkyl groups (as defined above). The number of carbon atoms in the alkyl groups is not particularly limited, and may range from 1 to 8 carbon atoms, preferably 1 to 4 carbon atoms. Representative examples of haloalkyl groups include, but are not limited to, chloroethyl, bromopropyl, fluoroethyl, trifluoroethyl, trichloroethyl, and trifluorobutyl.

The term lower alkoxy denotes lower alkyl groups (as defined above) attached via oxygen linkage to the rest of the molecule. Representative examples of lower alkoxy groups include, but are not limited to, are methoxy, ethoxy, isopropoxy, tert-butoxy, hexoxy, heptoxy, and octoxy.

The salt can be formed between a compound of formula I and a counter-ion of a phenoxy group of that compound. In a preferred embodiment, any pharmaceutically acceptable counter-ion may be used. Examples of suitable counter-ions include, but are not limited to, sodium, ammonium, and potassium. Compounds containing methylene functional groups can react with sodium bisulfite or sodium dithionite via Michael addition to form water-soluble salts as prodrugs.

In one embodiment of the invention, each of $X_1$, $X_2$, $X_3$, and $X_4$ in formula I is independently hydrogen, and $R_4$ is methylene, as represented by formula II:

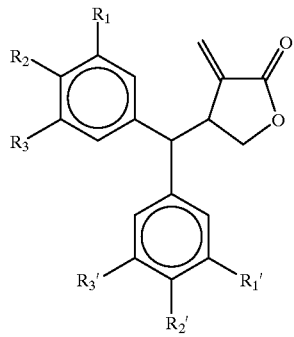

(II)

In another embodiment of the invention, $R_4$ in formula I is methylene, as represented by formula III:

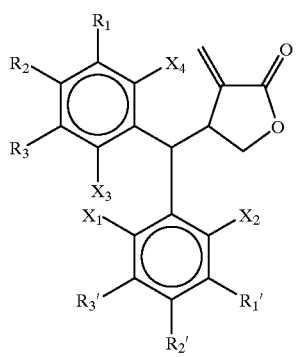

(III)

In another embodiment of the invention, $R_4$ in formula I is halomethyl, as represented by formula IV, where $X_5$ represents halogen:

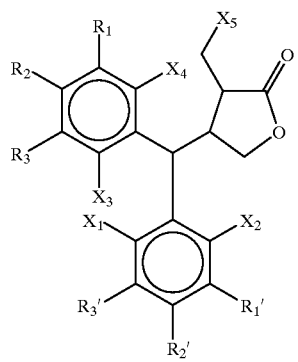

(IV)

The present invention includes all optical isomers covered by formulas I, II, III, and IV.

The present invention further provides a pharmaceutical composition containing an effective amount of at least one of the peperomin analogs of formula I or a pharmaceutically acceptable salt thereof, and a pharmaceutically acceptable carrier or excipient.

The present invention further provides a method of treating cancer, whether by direct treatment of cancer cells in a host organism or as prophylaxis. Examples of cancer that may be treated by the method of the present invention include, but are not limited to, leukemia, hepatocellular cancer, cervical cancer, epidermoid oral cancer, and colon cancer. The method includes the step of administering to a patient in need thereof an effective amount of a compound of formula I, or a pharmaceutically acceptable salt thereof. The present invention further provides a method of treating cancer, including the step of administering to a patient in need thereof a pharmaceutical composition containing an effective amount of at least one of the peperomin analogs of formula I or a pharmaceutically acceptable salt thereof, and a pharmaceutically acceptable carrier or excipient.

The compounds of formulae I–IV of this invention can be prepared by the following synthetic reactions (Reactions A, B, C, and D) starting from a precursor V. The preparation of a precursor V is described by Zee, et al. *Journal of the Chinese Chemical Society* 1990, 37, 583, the entire contents of which are incorporated herein by reference; and Cruz-Almanza, et al. *Heterocycles* 1992, 34, 2323, the entire contents of which are incorporated herein by reference.

As shown in Reaction A below, reacting butyrolactone of formula V with ethyl formate in the presence of a strong base (such as sodium hydride) yields a formylated butyrolactone of formula VI, where $R_1$, $R_2$, $R_3$, $R_1'$, $R_2'$, and $R_3'$ are as defined above.

Reaction A

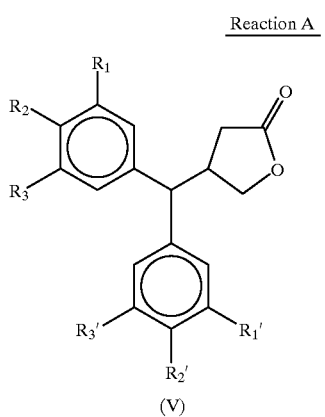

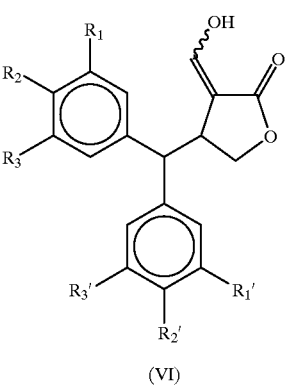

Reduction of formyl butyrolactone VI with sodium borohydride at a temperature of −30° C. provides the corresponding α-hydroxymethyl butyrolactone of formula VII (see reaction B below).

Reaction B

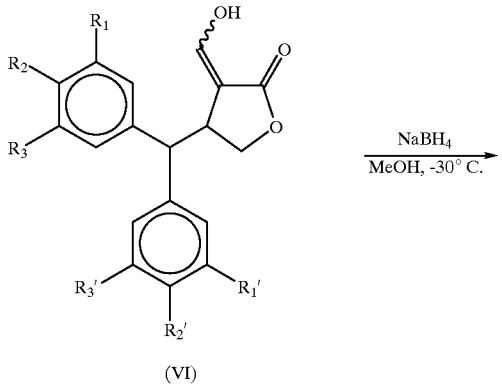

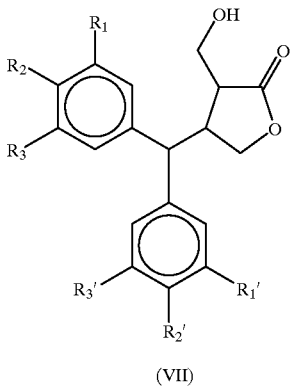

The methylene γ-butyrolactone of formula II is obtained via Reaction C (illustrated below) by reacting α-hydroxymethyl butyrolactone VII with methanesulfonic anhydride and triethylamine.

Reaction C

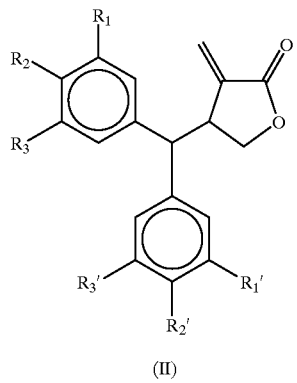

As shown in Reaction D below, the resulting methylene derivative from the above reaction is then reacted with a halogen to give halogenated derivatives III and IV. Halomethyl butyrolactone IV results from the addition reaction of byproduct hydrogen halide with halogenated derivative III.

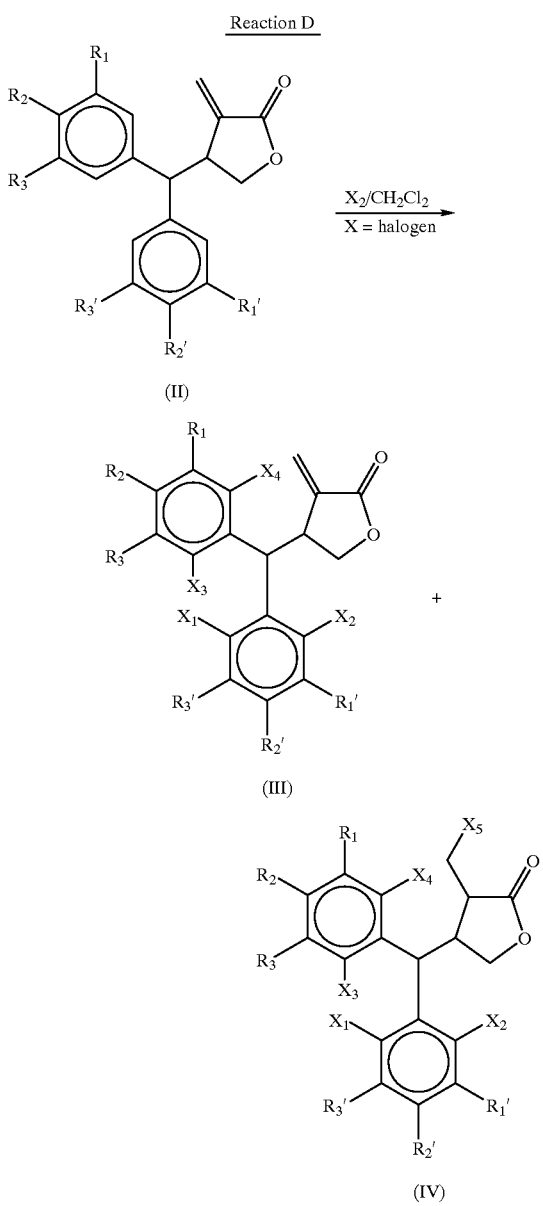

All of the compounds of formulas II, III, and IV prepared according to the present invention exhibited good in vitro anti-cancer activity towards various human tumor cell lines.

Optical isomers of formulas II, III, and IV can be synthesized starting from an optically active butyrolactone of formula V (See, Zee, et al. *Journal of Chinese Chemical Society* 1991, 38, 371, the entire contents of which are incorporated herein by reference). Thus the present invention includes all of the optical isomers covered by general formulas II, III, and IV.

As set forth above, in addition to pharmaceutical compositions containing an effective amount of a compound of formulae I–IV or a pharmaceutically acceptable salt thereof and a pharmaceutically acceptable carrier or excipient, the present invention also provides a method of treating cancer by administering to a patient an effective amount of said compositions.

As used in this disclosure, an effective amount of the compounds of formulae I–IV is defined as the amount of the compound which, upon administration to a patient in need thereof, inhibits growth of tumor cells, kills malignant cells, reduces the size of the tumors, or otherwise confers a therapeutic effect on the treated patient. The effective amount to be administered to a patient is typically based on body surface area, patient weight, and patient condition. The interrelationship of dosages for animals and humans (based on milligrams per meter squared of body surface) is described by Freireich, et al., *Cancer Chemother. Rep.* 1966, 50, 219, the entire contents of which are incorporated herein by reference. Body surface area may be approximately determined from height and weight of the patient. See, e.g., "Scientific Tables," Geigy Pharmaceuticals, Ardley, N.Y., 1970, 537, the entire contents of which are incorporated herein by reference. Effective doses will also vary, as recognized by those skilled in the art, dependant on the route of administration, excipient usage, and the possibility of co-usage with other therapeutic treatments, including use of other anti-tumor agents and radiation therapy.

The route of administration to patients is not particularly limited and includes any acceptable method. The pharmaceutical composition may be administered via the parenteral route, examples thereof including, but not limited to, subcutaneously, intraperitoneally, intramuscularly and intravenously. Examples of parenteral dosage forms include, but are not limited to, aqueous solutions of the active agent in an isotonic saline, 5% glucose, or other well-known pharmaceutically acceptable liquid carrier.

The compounds of formulae I–IV of the invention can also be formulated into dosage forms for other routes of administration utilizing well-known methods. The pharmaceutical composition can be formulated in dosage forms for oral administration; examples thereof include, but are not limited to, a capsule, gel seal, or tablet. Capsules may comprise any well-known pharmaceutically acceptable material such as gelatin or cellulose derivatives. Tablets may be formulated in accordance with the conventional procedure, e.g., by compressing mixtures of a compound of formulae I–IV and a solid carrier, and a lubricant. Examples of solid carriers include, but are not limited to, starch and sugar bentonite. The compound of formulae I–IV can also be administered in a form of a hard shell tablet or capsule containing, for example, lactose or mannitol as a binder, and a conventional filler and a tableting agent, or any other acceptable binders, fillers, or tableting agents.

The carrier in the pharmaceutical composition must be "acceptable" in the sense of being compatible with the active ingredient of the formulation and not deleterious to the patient. Preferably, the carrier is capable of stabilizing the active ingredient of the formulation.

The antitumor activity of the compound of formulae I–IV described above can be preliminarily evaluated using an in vitro assay, and then confirmed by in vivo testing. For example, see U.S. Pat. No. 5,578,636, the entire contents of which are incorporated herein by reference.

Representative examples of compounds of formula I of this invention include, but are not limited to:

Compound 1: 2-Methylene-3-[bis(3,4,5-trimethoxy)phenyl] methyl γ-butyrolactone.

Compound 2: 2-Bromomethyl-3-[bis(2-bromo-3,4,5-trimethoxy)phenyl]-methyl γ-butyrolactone*.

Compound 3: 2-Methylene-3-[1-(3,4-methylenedioxy) phenyl-1'-(3,4,5-trimethoxy)phenyl]methyl γ-butyrolactone.

Compound 4: 2-Bromomethyl-3-[bis(2-bromo-3,4,5-trimethoxy)phenyl]-methyl γ-butyrolactone*.

Compound 5: 2-Methylene-3-[1-(2(or 6)-bromo-3,4-methylenedioxy)-phenyl-1'-(2-bromo-3,4,5-trimethoxy) phenyl]methyl γ-butyrolactone.

Compound 6: 2-Methylene-3-[bis(2-bromo-3,4,5-trimethoxy)phenyl]methyl γ-butyrolactone.

Compound 7: 2-Methylene-3-[1-(3,4-methylenedioxy-5-methoxy)phenyl-1'-(3,4,5-trimethoxy)phenyl]methyl γ-butyrolactone.

Compound 8: 2-Bromomethyl-3-[1-(2(or 6)-bromo-3,4-methylenedioxy-5-methoxy)phenyl-1'-(2-bromo-3,4,5-trimethoxy)phenyl]methyl γ-butyrolactone.

Compound 9: 2-Bromomethyl-3-[1-(2(or 6)-bromo-3,4-methylenedioxy)-phenyl-1'-(2-bromo-3,4,5-trimethoxy)phenyl]methyl γ-butyrolactone.

*Compounds 2 and 4 are diastereoisomers, with respect to C-2 and C-3 of the butyrolactone ring. In Compound 2, the two substituents of the γ-butyrolactone moiety are trans to each other, while in Compound 4, they are cis to each other.

Compounds 1–9 were evaluated for in vitro cytotoxicity by the MTT assay, against four types of human tumor cell lines, including COLO 205, HA22T, SKBR$_3$, and MOLT-4.

COLO 205 was grown as a monolayer in RPMI 1640 (Gibco) with 10% fetal serum (FBS, Hyclon). HA22T/VGH was grown as a monolayer in DMEM/F12 medium (Gibco) supplemented with 10% FBS and 1 µM nonessential amino acid (Gibco, BRL). SKBr$_3$ was grown as a monolayer in DMEM/F12 medium (Gibco) with 10% FCS and 1% penicillin/streptomycin (Gibco, BRL). MOLT-4 was grown as a suspension cell line in RPMI 1640 supplemented with 10% FCS and 1% penicillin/streptomycin (Gibco, BRL). Exponentially growing cell cultures were maintained in a humidified incubator (NAPCO, Model 5410) with an atmosphere of 5% CO$_2$-95% air at 37° C.

In principle, the assay is dependent on the cellular reduction of MTT (Sigma Chemical Co.) by the mitochondrial dehydrogenase of viable cells to a dark blue formazan product. The viable cell number is directly proportional to the production of formazan, which can be measured spectrophotometrically following solubilization.

Single cell suspensions were obtained by mechanical disaggregation of the floating cell line (MOLT-4) and by trypsinization of the monolayer cultures (COLO 205, HA22T/VGH, SKBr$_3$) and counted by trypan blue exclusion. The cell suspensions (180 µl) were added into 96-well microtiter plates (Nunc 67008) using a multichannel pipette, and the incubation was allowed for 24 h.

Each test compound was dissolved in a 10% DMSO (Sigma, D-8779) and 90% DPBS solution. 20 µl of this solution was dispensed to each microtiter plate well, and diluted to give final concentrations ranging from 100 µg/ml to 0.01 µg/ml by 10-fold dilutions. The cells were then incubated in the presence of the drug (the test compound) for a further 72 h. At the end of this time, 20 µl of a MTT solution (5 mg/ml) was added to each well and the incubation was allowed a further 4 h. After this time, the culture plates containing suspension lines or any detached cells were centrifuged at a low speed of 1000 rpm for 5 min. 170 µl of the culture medium supernatant was removed from each well and replaced by 200 µl of DMSO. After the solubilization of formazans, the optical density was then read by an automated spectrophotometric plate reader (ELISA, Molecular Device Emax) at a wavelength of 545–690 nm. Readings were transferred to a microcomputer and final reports were generated using especially developed software.

TABLE 1

| | Cell Line | | | |
|---|---|---|---|---|
| Compound | COLO 205 IC$_{50}$ (µg/ml) | HA22T IC$_{50}$ (µg/ml) | SKBR$_3$ IC$_{50}$ (µg/ml) | MOLT-4 IC$_{50}$ (µg/ml) |
| 1 | 2.3 | 7.1 | 4.0 | 2.8 |
| 2 | 5.0 | 6.6 | 3.7 | 3.1 |
| 3 | 5.8 | 6.4 | 4.6 | 4.3 |
| 4 | 4.2 | 6.4 | 4.9 | 4.9 |
| 5 | 6.8 | 5.9 | 5.3 | 3.9 |
| 6 | 6.7 | 5.9 | 3.7 | 4.3 |
| 7 | 4.4 | 7.1 | 4.6 | 3.0 |
| 8 | 6.1 | 5.8 | 4.3 | 1.5 |
| 9 | 5.6 | 5.7 | 4.5 | 5.8 |
| DOXORUBICIN | 0.2 | 0.2 | 0.1 | 0.01 |

As shown in Table 1, all nine tested compounds were found to be active toward all testing cancer cell lines. A significant drawback of current anticancer drugs such as doxorubicin is hypersensitivity towards leukemia cells as compared to other solid tumor cells. The tested compounds, however, did not exhibit hypersensitivity to MOLT-4 leukemia cell line, as did the current chemotherapy drug (doxorubicin).

The present invention is further illustrated by the following examples, which are designed to teach those of ordinary skill in the art how to practice the invention. The following examples are illustrative of the invention and should not be construed as limiting the invention as claimed.

EXAMPLE 1

Preparation of 2-formyl-3-[bis(3,4,5-trimethoxy)phenyl]-methyl γ-butyrolactone

To an ice-cooled solution of butyrolactone of formula V where $R_1=R_2=R_3=R_1'=R_2'=R_3'=OCH_3$ (5.79 mmol) in dry ethyl formate (26 ml) was added sodium hydride (0.62 g, 25.8 mmol) portionwise. After removing the ice-bath, the reaction mixture was stirred at room temperature for 1 h. After this, the reaction mixture was poured into ice-water, acidified with a 3N hydrochloride solution, and extracted with chloroform. The extract was washed with water and dried. After evaporation of the solvent under reduced pressure, the residue was purified over silica gel column using ethylacetate/n-hexane (1:1) as an eluent to obtain 2.14 g (78% yield) of α-formyl lactone of formula V where

$^1$H NMR (CDCl$_3$, 500 MHz): δ10.42 (br s, 0.55H), 9.52 (br s, 0.45H), 6.45 (m, 4H), 6.03 (s, 0.55H), 4.34 (dd, J=9.2, 8.8 Hz, 0.55H), 4.25 (dd, J=8.8, 8.0 Hz, 0.45H), 4.02 (m, 1H), 3.74 (d, J=12.0 Hz, 1H), 3.46 (d, J=4.8 Hz, 0.45H); MS (m/z): 460 (M$^+$, 50), 347 (100).

EXAMPLE 2

Preparation of 2-formyl-3-[1-(3,4-methylenedioxy-5-methoxy)phenyl-1'-(3,4,5-trimethoxy)phenyl] methyl γ-butyrolactone Following the same procedure of Example 1, the above-titled compound (VI; $R_1=R_2=R_3=R_3'=OCH_3$; $R_1'$, $R_2'=-OCH_2O-$) as a mixture of diastereoisomers was prepared from the butyrolactone of formula V where $R_1=R_2=R_3=R_3'=OCH_3$; $R_1'$, $R_2'=-OCH_2O-$.

$^1$H NMR (CDCl$_3$, 500 MHz): δ9.60 (d, J=4.80 Hz, 1H), 6.41–6.50 (m, 4H), 5.92–5.96 (m, 2H), 4.40 (m, 1H), 4.15 (m, 1H), 3.80–3.90 (m, 12H), 3.70 (m, 1H), 3.50 (m, 1H); MS (m/z): 444 (M+, 15), 379 (100).

EXAMPLE 3

Preparation of 2-formyl-3-[1-(3,4-methylenedioxy)-phenyl-1'-(3,4,5-trimethoxy)phenyl]methyl γ-butyrolactone Following the same procedure of Example 1, the above-titled compound (VI; $R_1$, $R_2$=—$OCH_2O$—; $R_3$=H, $R_1'$=$R_2'$=$R_3'$=$OCH_3$) as a mixture of diastereoisomers was prepared from the butyrolactone of formula V where $R_1$, $R_2$=—$OCH_2O$—; $R_3$=H; $R_1'$, $R_2'$, $R_3'$=$OCH_3$.

$^1$H NMR (CDCl$_3$, 200 MHz): δ9.58 (d, J=9.7 Hz, 1H), 6.70–6.80 (m, 3H), 6.44 (s, 2H), 5.95 (s, 2H), 4.34 (m, 1H), 4.07 (m, 1H), 3.81–3.86 (m, 9H), 3.75 (d, J=12.0 Hz, 1H), 3.49 (m, 1H).

EXAMPLE 4

Preparation of 2-hydroxymethyl-3-[bis(3,4,5-trimethoxy)phenyl]methyl γ-butyrolactone To a methanol (30 ml) solution of the α-formyl lactone (5.65 mmol) of Example 1 at −30° C. was added sodium borohydride (0.18 g, 4.76 mmol). The reaction mixture was allowed to stir at room temperature for 1 h. After this time, the mixture was acidified with a 3N hydrochloride solution and methanol was evaporated under reduced pressure. The residue was treated with dichloromethane and water, and then the organic layer was collected and dried over anhydrous magnesium sulfate. Evaporation of the solvent furnished an oily residue which was purified over silica gel column using ethylacetate/n-hexane (1:1) as an eluent to obtain 1.77 g (68% yield) of α-hydroxymethyl lactone of formula VII where $R_1$=$R_2$=$R_3$=$R_1'$=$R_2'$=$R_3'$=$OCH_3$.

$^1$H NMR (CDCl$_3$, 500 MHz): δ6.50 (s, 2H), 6.49 (s, 2H), 4.29 (dd, J=9.3, 8.2 Hz, 1H), 3.87 (dd, J=9.3, 8.2 Hz, 1H), 3.78, 3.82, 3.84 (each s, 18H), 3.74 (t, J=3.0 Hz, 0.5H), 3.71 (t, J=3.0 Hz, 0.5H), 3.66 (d, J=11.6 Hz, 1H), 3.41 (m, 1H), 3.16 (m, 1H), 2.45 (m, 1H), 2.25 (m, 1H); MS (m/z): 462 (M$^+$, 100), 347 (45).

EXAMPLE 5

Preparation of 2-hydroxymethyl-3-[1-(3,4-methylene-dioxy-5-methoxy)phenyl-1'-(3,4,5-trimethoxy)phenyl]methyl γ-butyrolactone Following the same procedure of Example 4, the above-titled compound (VII; $R_1$=$R_2$=$R_3$=$R_3'$=$OCH_3$; $R_1'$, $R_2'$=—$OCH_2O$—) as a mixture of diastereoisomers was prepared from the a-formyl lactone of Example 2.

$^1$H NMR (CDCl$_3$, 500 MHz): δ6.50–6.55 (m, 4H), 5.98 (s, 2H), 4.38 (m, 1H), 4.10–4.20 (m, 1H), 3.95, 3.90, 3.83 (each s, 12H), 3.80 (m, 1H), 3.72 (d, J=8.0 Hz, 1H), 3.45 (m, 1H), 3.30 (m, 1H), 2.45 (m, 1H); MS (m/z): 446 (M$^+$, 24), 416 (7), 331 (100).

EXAMPLE 6

Preparation of 2-hydroxymethyl-3-[1-(3,4-methylenedioxy)phenyl-1'-(3,4,5-trimethoxy)phenyl] methyl γ-butyrolactone Following the same procedure of Example 4, the above-titled compound (VII; $R_1$, $R_2$=—$OCH_2O$—; $R_3$=H; $R_1'$=$R_2'$=$R_3'$=$OCH_3$) as a mixture of diastereoisomers was prepared from the α-formyl lactone of Example 3.

$^1$H NMR (CDCl$_3$, 500 MHz): δ6.70–6.80 (m, 3H), 6.48 (m, 2H), 5.93 (m, 2H), 4.40 (m, 1H), 4.05 (m, 1H), 3.70 (m, 1H), 3.45 (m, 1H), 3.30 (m, 1H), 2.42 (m, 1H).

EXAMPLE 7

Preparation of 2-methylene-3-[bis(3,4,5-trimethoxy)-phenyl]methyl γ-butyrolactone To a solution of the 2-hydroxymethyl lactone of Example 4 in tetrahydrofuran (3 ml) and chloroform (1 ml) at −30° C. was added successfully triethylamine (0.46 g, 3.96 mmol), 4-dimethylaminopyridine (0.033 g, 0.27 mmol) and methanesulfonic anhydride (0.46 g, 2.64 mmol). The reaction mixture was allowed to stir at −30° C. for 10 min, then 0° C. for 3 h, and finally at room temperature for 12 h. After this time, the solvents were evaporated and the residue was treated with chloroform and water. The aqueous layer was separated and the organic layer was dried over anhydrous magnesium sulfate and concentrated. The residue was purified over silica gel column using acetone/ethylacetate/n-hexane (2:5:2) as an eluent to obtain 0.28 g (73%) of 2-methylene lactone of formula II where $R_1$=$R_2$=$R_3$=$R_1'$=$R_2'$=$R_3'$=$OCH_3$ as white needles (mp 156–158° C.).

$^1$H NMR (CDCl$_3$, 400 MHz): δ6.46 (s, 4H), 6.13 (s, 1H), 4.84 (s, 1H), 3.90 (m, 1H), 3.80, 3.82, 3.83 (each s, 18H), 4.30 (dd, J=9.4, 7.8 Hz, 1H), 4.00 (dd, J=9.5, 4.5 Hz, 1H), 3.71 (d, J=11 Hz, 1H); MS (m/z): 444 (M$^+$, 20), 347 (100).

EXAMPLE 8

Preparation of 2-methylene-3-[1-(3,4-methylenedioxy-5-methoxy)phenyl-1'-(3,4,5-trimethoxy)phenyl]methyl γ-butyrolactone Following the same procedure of Example 7, the above-titled compound (II; $R_1$=$R_2$=$R_3$=$R_3'$=$OCH_3$; $R_1'$, $R_2'$=—$OCH_2O$—) as a mixture of diastereoisomers was prepared from the 2-hydroxymethyl lactone of Example 5.

$^1$H NMR (CDCl$_3$, 500 MHz): δ6.50 (m, 1H), 6.47 (s, 1H), 6.44 (m, 1H), 6.16, 6.17 (each s, 1H), 5.98 (s, 2H), 4.90, 4.97 (each s, 1H), 4.36 (m, 1H), 4.03 (m, 1H), 3.93, 3.88, 3.86 (each s, 12H), 3.83 (m, 1H), 3.74 (d, J=7.2 Hz, 1H); MS (m/z): 428 (M$^+$, 8), 331 (100).

EXAMPLE 9

Preparation of 2-methylene-3-[1-(3,4-methylenedioxy)phenyl-1'-(3,4,5-trimethoxy)phenyl] methyl γ-butyrolactone Following the same procedure of Example 7, the above-titled compound (II; $R_1$, $R_2$=—$OCH_2O$—; $R_3$=H; $R_1'$=$R_2'$=$R_3'$=$OCH_3$) as a mixture of diastereoisomers was prepared from the 2-hydroxymethyl lactone of Example 6.

$^1$H NMR (CDCl$_3$, 500 MHz): δ6.73–6.76 (m, 3H), 6.44 (s, 2H), 6.14, 6.15 (each s, 1H), 5.95 (s, 2H), 4.88, 4.90 (each s, 1H), 4.34 (m, 1H), 4.00 (m, 1H), 3.86, 3.84, 3.81 (each s, 9H), 3.80 (m, 1H), 3.74 (d, J=7.2 Hz, 1H); MS (m/z): 398 (M$^+$, 20), 301 (100).

EXAMPLE 10

Preparation of 2-methylene-3-[bis(2-bromo-3,4,5-trimethoxy)phenyl]methyl γ-butyrolactone and 2-bromomethyl-3-[bis(3,4,5-trimethoxy)phenyl]methyl γ-butyrolactone To a solution of the 2-methylene lactone (0.2 g, 0.45 mmol) of Example 7 in dichloromethane (25 ml) was added bromine (0.075 g, 0.47 mmol) and the mixture was stirred at room temperature for 16 h. After this time, the reaction mixture was washed with 10% potassium carbonate solution and water, and dried over anhydrous magnesium sulfate. After evaporation of the solvent under reduced pressure, the residue was chromatographed on TLC films using ethylacetate/n-hexane (1:5) as an eluent to afford three compounds A (0.184 g, 60%), B (0.074 g, 24%), and C (0.022 g, 8%). Compound A and compound B were diastereoisomers of bromomethyl lactone of formula IV where $R_1=R_2=R_3=R_{1'=R2}'=R_3'=OCH_3$; $X_1=X_3=Br$; $X_2=X_4=H$; $X_5=Br$. Compound C was methylene lactone of formula III where $R_1=R_2=R_3=R_1'=R_2'=R_3'=OCH_3$; $X_1=X_3=Br$; $X_2=X_4=H$.

Compound A (mp 178.5–179° C.): $^1$H NMR (CDCl$_3$, 200 MHz): δ7.23 (s, 1H), 6.78 (s, 1H), 5.64 (d, J=11.0 Hz, 1H), 4.45 (m, 1H), 4.12 (d, J=10.4 Hz, 1H), 4.10 (m, 1H), 4.07 (s, 3H), 3.80–3.93 (m, 16H), 3.60 (m, 1H), 3.19 (d, J=10.4 Hz, 1H); $^{13}$C NMR (CDCl$_3$, 500 MHz): δ171.7 (s), 153.0 (s), 152.4 (s), 151.7 (s), 151.1 (s), 143.1 (s), 142.9 (s), 133.6 (s), 133.3 (s), 113.0 (s), 112.0 (d), 108.4 (d), 107.5 (s), 68.1 (t), 61.2 (q), 61.1 (q), 61.0 (q), 60.9 (q), 60.0 (d), 56.7 (q), 56.1 (q), 49.6 (d), 46.2 (d), 33.8 (t).

Compound B (mp 174.5–174.7° C.): $^1$H NMR (CDCl$_3$, 500 MHz): δ7.13 (s, 1H), 6.76 (s, 1H), 5.81 (d, J=10.7 Hz, 1H), 4.58 (m, 1H), 4.07 (d, J=10.6 Hz, 1H), 4.04 (m, 1H), 3.83–3.94 (m, 17H), 3.81 (s, 3H), 3.66 (d, J=10.6 Hz, 1H); $^{13}$C NMR (CDCl$_3$, 500 MHz): δ173.0 (s), 153.0 (s), 152.0 (s), 151.4 (s), 151.2 (s), 143.0 (s), 142.8 (s), 133.6 (s), 133.2 (s), 112.6 (s), 112.3 (d), 110.1 (d), 69.3 (t), 61.1 (q), 61.0 (q), 60.9 (q), 56.5 (d), 56.4 (q), 56.1 (q), 52.0 (d), 46.3 (d), 31.0 (t).

Compound C: $^1$H NMR (CDCl$_3$, 500 MHz): δ6.68, 6.66 (each s, 2H), 6.20 (s, 1H), 5.11 (d, J=10.0 Hz, 1H), 4.87 (s, 1H), 4.35 (m, 1H), 4.17 (m, 1H), 3.85–3.93 (m, 16H), 3.81 (s, 3H); MS (m/z): 602 (M$^+$, 10), 522 (30), 505 (84), 426 (16), 395 (52), 345 (100).

EXAMPLE 11

Preparation of 2-methylene-3-[1-(2(or 6)-bromo-3,4-methylenedioxy-5-methoxy)phenyl-1'-(2-bromo-3,4,5-trimethoxy)phenyl]methyl γ-butyrolactone and 2-bromomethyl-3-[1-(2(or 6)-bromo-3,4-methylenedioxy-5-methoxy)phenyl-1'-(2-bromo-3,4,5-trimethoxy)phenyl]methylγ-butyrolactone To a solution of the 2-methylene lactone (0.2 g, 0.45 mmol) of Example 8 in dichloromethane (26 ml) was added bromine (0.093 g, 0.58 mmol) and the mixture was stirred at room temperature for 21 h. After this time, the reaction mixture was washed with 10% potassium carbonate solution and water, and dried over anhydrous magnesium sulfate. After evaporation of the solvent under reduced pressure, the residue was chromatographed on TLC films using ethylacetate/n-hexane (1:5) as an eluent to afford compounds D (0.19 g, 60.6%) and E (0.04 g, 14.5%). Compound D was comprised of diastereoisomers of a bromomethyl lactone of formula IV where $R_1=R_2=R_3=R_3'=OCH_3$, $R_1'$; $R_2'=-OCH_2O-$; and $X_1=X_3=X_5=Br$, $X_2=X_4=H$ or $X_2=X_3=X_5=Br$, $X_1=X_4=H$. Compound E was a methylene lactone of formula III where $R_1=R_2=R_3=R_3'=OCH_3$; $R_1'$, $R_2'=-OCH_2O-$; and $X_1=X_3=Br$, $X_2=X_4=H$, or $X_2=X_3=Br$, $X_1=X_4=H$.

Compound D: $^1$H NMR (CDCl$_3$, 500 MHz): δ7.19 (m, 1H), 6.65 (m, 1H), 6.10, 6.60 (each d, J=20.0 Hz, 2H), 5.65 (d, J=11.0 Hz, 1H), 4.45 (m, 1H), 4.09–4.16 (m, 7H), 3.80–3.95 (m, 8H), 3.61 (m, 1H), 3.22 (m, 1H); MS (m/z): 666 (M$^+$, 5), 586 (10, M$^+$—HBr), 505 (16), 489 (24), 426 (40), 329 (100).

Compound E: $^1$H NMR (CDCl$_3$, 500 MHz): δ6.65 (m, 1H), 6.18 (s, 1H), 6.62–6.65 (m, 1H), 6.55–6.60 (m, 1H), 6.18 (s, 1H), 6.00–6.10 (m, 2H), 5.04 (d, J=10.7 Hz, 1H), 4.82 (s, 1H), 4.32 (m, 1H), 4.15 (m, 1H), 3.80–4.09 (m, 13H).

EXAMPLE 12

Preparation of 2-methylene-3-[1-(2(or 6)-bromo-3,4-methylenedioxy)phenyl-1'-(2-bromo-3,4,5-trimethoxy)-phenyl]methyl γ-butyrolactone and 2-bromomethyl-3-[1-(2(or 6)-bromo-3,4-methylenedioxy)phenyl-1'-(2-bromo-3,4,5-trimethoxy)phenyl]methyl γ-butyrolactone To a solution of the 2-methylene lactone (0.14 g, 0.35 mmol) of Example 9 in dichloromethane (20 ml) was added bromine (0.06 g, 0.33 mmol) and the mixture was stirred at room temperature for 18 h. After this time, the reaction mixture was washed with 10% potassium carbonate solution and water, and dried over anhydrous magnesium sulfate. After evaporation of the solvent under reduced pressure, the residue was chromatographed on TLC films using ethylacetate/n-hexane (1:5) as an eluent to afford compounds F (0.07 g, 31.4%) and G (0.083 g, 42.6%). Compound F was comprised of diastereoisomers of bromomethyl lactone of formula IV where $R_1$, $R_2=-OCH_2O-$; $R_3=H$, $R_1'=R_2'=R_3'=OCH_3$; and $X_1=X_3=X_5=Br$, $X_2=X_4=H$, or $X_1=X_4=X_5=Br$, $X_2=X_3=H$. Compound G was methylene lactone of formula III where $R_1$, $R_2=-OCH_2O-$; $R_3=H$; $R_1'$, $R_2'$, $R_3'=OCH_3$; and $X_1=X_3=Br$, $X_2=X_4=H$. or $X_1=X_4=Br$, $X_2=X_3=H$.

Compound F: $^1$H NMR (CDCl$_3$, 500 MHz): δ7.03 (m, 1H), 6.94 (m, 1H), 6.76 (m, 1H), 5.95 (m, 2H), 4.82, 5.00 (each d, J=11.0 Hz, 1H), 4.05–4.12 (m, 2H), 4.02 (s, 3H), 3.85–3.92 (m, 8H), 3.70 (m, 1H), 2.90, 3.12 (each d, J=10.4 Hz, 1H).

Compound G: $^1$H NMR (CDCl$_3$, 500 MHz): δ6.68–6.82 (m, 3H), 6.09, 6.16 (each s, 1H), 5.94 (s, 2H), 4.82, 4.88 (each s, 1H), 4.50, 4.65 (each d, J=11.4 Hz, 1H), 4.32 (m, 1H), 4.05 (m, 1H), 3.82–3.88 (m, 9H).

The foregoing written description relates to various embodiments of the present invention. Numerous changes and modifications may be made therein without departing from the spirit and scope of the invention as defined in the following claims.

What is claimed is:

1. A compound of the formula I:

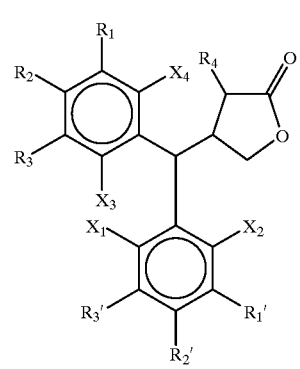

(I)

wherein
$R_1$, $R_2$, $R_3$, $R_1'$, $R_2'$, and $R_3'$ are independently the same or different and each represent hydrogen, hydroxy, or lower alkoxy, or any vicinal two of $R_1$, $R_2$, $R_3$, $R_1'$, $R_2'$, and $R_3'$ together represent $-O-(CH_2)_n-O-$, wherein n=1 or 2, $R_4$ represents methylene or halomethyl, and $X_1$, $X_2$, $X_3$, and $X_4$ are independently the same or different and each represent hydrogen or halogen, or a salt thereof, provided that when $R_4$ represents methylene, (a) $X_1$, $X_2$, $X_3$, and $X_4$ each represent hydrogen, and $R_1$, $R_2$, $R_3$, $R_1'$, $R_2'$, and $R_3'$ each represent methoxy: or (b) $X_1$ and $X_3$ each represent halogen, $X_2$ and $X_4$ each represent hydrogen, and $R_1$, $R_2$, $R_3$, $R_1'$, $R_2'$, and $R_3'$ each represent methoxy.

2. A compound of the formula I as claimed in claim 1, wherein $X_1$, $X_2$, $X_3$, and $X_4$ each represent hydrogen and $R_4$ represents methylene.

3. A compound of the formula I as claimed in claim 2, wherein $R_1$, $R_2$, $R_3$, $R_1'$, $R_2'$, and $R_3'$ each represent methoxy.

4. A compound of the formula I as claimed in claim 1, wherein $R_4$ represents methylene.

5. A compound of the formula I as claimed in claim 4, wherein $X_1$ and $X_3$ each represent halogen, $X_2$ and $X_4$ each represent hydrogen, and $R_1$, $R_2$, $R_3$, $R_1'$, $R_2'$, and $R_3'$ each represent methoxy.

6. A compound of the formula I as claimed in claim 1, wherein $R_4$ represents halomethyl.

7. A compound of the formula I as claimed in claim 6, wherein $R_1$ and $R_2$ together represent —O—CH$_2$—O—, $R_3$ represents hydrogen, $R_1'$, $R_2'$, and $R_3'$ each represent methoxy, $X_1$ and $X_3$ each represent halogen, and $X_2$ and $X_4$ each represent hydrogen.

8. A compound of the formula I as claimed in claim 1, wherein the compound is 2-methylene-3-[bis(3,4,5-trimethoxy)phenyl]methyl γ-butyrolactone; 2-bromomethyl-3-[bis(2-bromo-3,4,5-trimethoxy)phenyl]-methyl γ-butyrolactone; 2-methylene-3-[1-(3,4-methylenedioxy)phenyl-1'-(3,4,5-trimethoxy)phenyl] methyl γ-butyrolactone; 2-methylene-3-[1-(2(or 6)-bromo-3,4-methylenedioxy)-phenyl-1'-(2-bromo-3,4,5-trimethoxy)phenyl]methyl γ-butyrolactone; 2-methylene-3-[bis(2-bromo-3,4,5-trimethoxy)phenyl]methyl γ-butyrolactone; 2-methylene-3-[1-(3,4-methylenedioxy-5-methoxy)phenyl-1'-(3,4,5-trimethoxy)phenyl]methyl γ-butyrolactone; 2-bromomethyl-3-[1-(2(or 6)-bromo-3,4-methylenedioxy-5-methoxy)phenyl-1'-(2-bromo-3,4,5-trimethoxy)phenyl] methyl γ-butyrolactone; or 2-bromomethyl-3-[1-(2(or 6)-bromo-3,4-methylenedioxy)-phenyl-1'-(2-bromo-3,4,5-trimethoxy)phenyl]methyl γ-butyrolactone.

9. A pharmaceutical composition comprising an effective amount of a compound of the formula I:

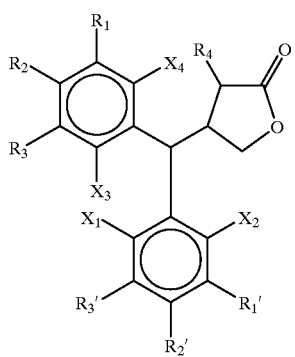

(I)

wherein
$R_1$, $R_2$, $R_3$, $R_1'$, $R_2'$, and $R_3'$ are independently the same or different and each represent hydrogen, hydroxy, or lower alkoxy, or any vicinal two of $R_1$, $R_2$, $R_3$, $R_1'$, $R_2'$, and $R_3'$ together represent —O—(CH$_2$)$_n$—O—, wherein n=1 or 2,
$R_4$ represents methylene or halomethyl, and
$X_1$, $X_2$, $X_3$, and $X_4$ are independently the same or different and each represent hydrogen or halogen, or a pharmaceutically acceptable salt thereof; and a pharmaceutically acceptable carrier or excipient;

provided that when $R_4$ represents methylene, (a) $X_1$, $X_2$, $X_3$, and $X_4$ each represent hydrogen, and $R_1$, $R_2$, $R_3$, $R_1'$, $R_2'$, and $R_3'$ each represent methoxy; or (b) $X_1$ and $X_3$ each represent halogen, $X_2$ and $X_4$ each represent hydrogen, and $R_1$, $R_2$, $R_3$, $R_1'$, $R_2'$, and $R_3'$ each represent methoxy.

10. The pharmaceutical composition of claim 9, wherein $X_1$, $X_2$, $X_3$, and $X_4$ each represent hydrogen and $R_4$ represents methylene.

11. The pharmaceutical composition of claim 10, wherein $R_1$, $R_2$, $R_3$, $R_1'$, $R_2'$, and $R_3'$ each represent methoxy.

12. The pharmaceutical composition of claim 9, wherein $R_4$ represents methylene.

13. The pharmaceutical composition of claim 12, wherein $X_1$ and $X_3$ each represent halogen, $X_2$ and $X_4$ each represent hydrogen, and $R_1$, $R_2$, $R_3$, $R_1'$, $R_2'$, and $R_3'$ each represent methoxy.

14. The pharmaceutical composition of claim 9, wherein $R_4$ represents halomethyl.

15. The pharmaceutical composition of claim 14, wherein $R_1$ and $R_2$ together represent —O—CH$_2$—O—, $R_3$ represents hydrogen, $R_1'$, $R_2'$, and $R_3'$ each represent methoxy, $X_1$ and $X_3$ each represent halogen, and $X_2$ and $X_4$ each represent hydrogen.

16. The pharmaceutical composition of claim 9, wherein the compound of the formula I is 2-methylene-3-[bis(3,4,5-trimethoxy)phenyl]methyl γ-butyrolactone; 2-bromomethyl-3-[bis(2-bromo-3,4,5-trimethoxy)phenyl]-methyl γ-butyrolactone; 2-methylene-3-[1-(3,4-methylenedioxy)phenyl-1'-(3,4,5-trimethoxy)phenyl] methyl γ-butyrolactone; 2-methylene-3-[1-(2(or 6)-bromo-3,4-methylenedioxy)-phenyl-1'-(2-bromo-3,4,5-trimethoxy) phenyl]methyl γ-butyrolactone; 2-methylene-3-[bis(2-bromo-3,4,5-trimethoxy)phenyl]methyl γ-butyrolactone; 2-methylene-3-[1-(3,4-methylenedioxy-5-methoxy)phenyl-1'-(3,4,5-trimethoxy)phenyl]methyl γ-butyrolactone; 2-bromomethyl-3-[1-(2(or 6)-bromo-3,4-methylenedioxy-5-methoxy)phenyl-1'-(2-bromo-3,4,5-trimethoxy)phenyl] methyl γ-butyrolactone; or 2-bromomethyl-3-[1-(2(or 6)-bromo-3,4-methylenedioxy)-phenyl-1'-(2-bromo-3,4,5-trimethoxy)phenyl]methyl γ-butyrolactone.

17. A method for treatment of leukemia, hepatocellular cancer, cervical cancer, epidermoid oral cancer, or colon cancer comprising administering to a patient in need thereof an effective amount for said treatment of a compound of the formula I:

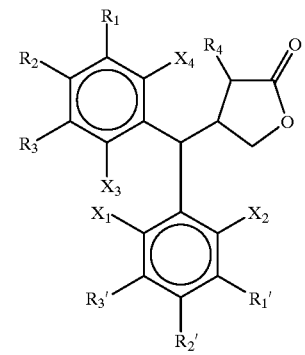

(I)

wherein
$R_1$, $R_2$, $R_3$, $R_1'$, $R_2'$, and $R_3'$ are independently the same or different and each represent hydrogen, hydroxy, or lower alkoxy, or any vicinal two of $R_1$, $R_2$, $R_3$, $R_1'$, $R_2'$, and $R_3'$ together represent —O—(CH$_2$)$_n$—O—, wherein n=1 or 2,
$R_4$ represents methylene or halomethyl, and $X_1$, $X_2$, $X_3$, and $X_4$ are independently the same or different and each represent hydrogen or halogen, or a pharmaceutically acceptable salt thereof.

18. The method of claim 17, wherein $X_1$, $X_2$, $X_3$, and $X_4$ each represent hydrogen and $R_4$ represents methylene.

19. The method of claim 18, wherein $R_1$, $R_2$, $R_3$, $R_1'$, $R_2'$, and $R_3'$ each represent hydrogen.

20. The method of claim 17, wherein $R_4$ represents methylene.

21. The method of claim 20, wherein $X_1$ and $X_3$ each represent halogen, $X_2$ and $X_4$ each represent hydrogen, and $R_1$, $R_2$, $R_3$, $R_1'$, $R_2'$, and $R_3'$ each represent methoxy.

22. The method of claim 17, wherein $R_4$ represents halomethyl.

23. The method of claim 22, wherein $R_1$ and $R_2$ together represent —O—$CH_2$—O—, $R_3$ represents hydrogen, $R_1'$, $R_2'$, and $R_3'$ each represent methoxy, $X_1$ and $X_3$ each represent halogen, and $X_2$ and $X_4$ each represent hydrogen.

24. The method of claim 17, wherein the compound of the formula I is 2-methylene-3-[bis(3,4,5-trimethoxy)phenyl]methyl γ-butyrolactone; 2-bromomethyl-3-[bis(2-bromo-3,4,5-trimethoxy)phenyl]-methyl γ-butyrolactone; 2-methylene-3-[1-(3,4-methylenedioxy)phenyl-1'-(3,4,5-trimethoxy)phenyl]methyl γ-butyrolactone; 2-methylene-3-[1-(2(or 6)-bromo-3,4-methylenedioxy)-phenyl-1'-(2-bromo-3,4,5-trimethoxy)phenyl]methyl γ-butyrolactone; 2-methylene-3-[bis(2-bromo-3,4,5-trimethoxy)phenyl]methyl γ-butyrolactone; 2-methylene-3-[1-(3,4-methylenedioxy-5-methoxy)phenyl-1'-(3,4,5-trimethoxy)phenyl]methyl γ-butyrolactone; 2-bromomethyl-3-[1-(2(or 6)-bromo-3,4-methylenedioxy-5-methoxy)phenyl-1'-(2-bromo-3,4,5-trimethoxy)phenyl]methyl γ-butyrolactone; or 2-bromomethyl-3-[1-(2( or 6)-bromo-3,4-methylenedioxy)-phenyl-1'-(2-bromo-3,4,5trimethoxy)phenyl]methyl γ-butyrolactone.

* * * * *